(12) United States Patent
Hirota et al.

(10) Patent No.: US 7,928,367 B2
(45) Date of Patent: Apr. 19, 2011

(54) METHODS OF PREPARING SAMPLES FOR MALDI MASS SPECTROMETRY AND REAGENT COMPOSITIONS FOR THE SAME

(75) Inventors: Hiroshi Hirota, Yokohama (JP);
Miwako Asanuma, Yokohama (JP);
Seketsu Fukuzawa, Yokohama (JP);
Shigeyuki Yokoyama, Yokohama (JP)

(73) Assignee: Riken, Saitama (JP)

( * ) Notice: Subject to any disclaimer, the term of this patent is extended or adjusted under 35 U.S.C. 154(b) by 656 days.

(21) Appl. No.: 11/772,799

(22) Filed: Jul. 2, 2007

(65) Prior Publication Data
US 2008/0067343 A1    Mar. 20, 2008

Related U.S. Application Data

(63) Continuation of application No. PCT/JP2006/300002, filed on Jan. 4, 2006.

(30) Foreign Application Priority Data

Jan. 7, 2005    (JP) .................................. 2005-002954

(51) Int. Cl.
*B01D 59/44*    (2006.01)
(52) U.S. Cl. ........................ 250/288; 250/282; 250/297
(58) Field of Classification Search .................... 250/288
See application file for complete search history.

(56) References Cited

U.S. PATENT DOCUMENTS

| | | | |
|---|---|---|---|
| 6,316,266 B1 | 11/2001 | Nelson | |
| 6,569,383 B1 | 5/2003 | Nelson et al. | |
| 6,822,230 B2* | 11/2004 | Schleifer et al. | 250/288 |
| 7,282,475 B2* | 10/2007 | Porter et al. | 510/424 |
| 7,488,603 B2* | 2/2009 | Gjerde et al. | 436/177 |
| 2005/0037516 A1 | 2/2005 | Schmucker et al. | |
| 2006/0214104 A1* | 9/2006 | Pope et al. | 250/297 |

FOREIGN PATENT DOCUMENTS

WO    WO 03/021267    3/2003

OTHER PUBLICATIONS

Zhang et al., "Matrix-assisted laser desorption/ionization mass spectrometry using porous silicon and silca gel as matrix", Rapid Communications in Mass Spectrometry, (2001), 15, pp. 217-223.

(Continued)

*Primary Examiner* — Phillip A Johnston
(74) *Attorney, Agent, or Firm* — Birch, Stewart, Kolasch & Birch, LLP

(57) ABSTRACT

A simple and efficient method of preparing a sample in the measurement according to matrix-assisted laser desorption/ionization mass spectrometry (MALDI-MS) capable of inhibiting any ion suppression by impurities, such as inorganic salts and surfactants, contained in the sample. An analyte and matrix molecules are co-crystallized in the presence of porous microparticles. Preferably, this co-crystallization is carried out by bringing the analyte, matrix molecules and porous microparticles into contact with each other on a target plate and thereafter drying the mixture. The porous microparticles consist of an ion exchanger having an average particle diameter of not more than 50 μm, preferably a strongly basic anion exchanger.

18 Claims, 4 Drawing Sheets

OTHER PUBLICATIONS

Fukuzawa et al., "On-Probe Sample Preparation without Washes for Matrix-Assisted Laser Desorption/Ionization Mass Spectrometry Using an Anion Exchange Medium", Anal. Chem (2005), 77, pp. 5750-5754.

Brockman et al., "A Desalting Approach for MALDI-MS Using On-Probe Hydrophobic Self-Assembled Monolayers", Anal. Chem. (1997), 69, pp. 4716-4720.

Warren et al., "On-Probe Solid-Phase Extraction/MALDI-MS Using Ion-Pairing Interactions for the Cleanup of Peptides and Proteins", Anal. Chem. (1998), 70, pp. 3757-3761.

Lee, C.H., et al., "Further Exploration of Novel On-Target Sample Preparation Methods Using Polymeric Substrates," Proceedings of the 50th ASMS Conference on Mass Spectrometry and Allied topics, pp. 627-628 (2002).

Rosinke, B., et al., "Matrix-Assisted Laser Desorption/Ionization Mass Spectrometry (MALDI-MS) of Membrane Proteins and Non-covalent Complexes," J. Mass Spectrometry, vol. 30, pp. 1462-1468 (1995).

Rajnarayanan, Rajendram V., et al., Ion-pair assisted recovery of matrix-assisted laser desorption/ionization mass spectral signals from SDS-containing peptide-protein mixtures, Journal of Mass Spectrometry, vol. 39, pp. 79-85 (2004).

Rouse, Jason C., et al., On-the-Probe Sample Cleanup Strategies for Glycoprotein-Released Carbohydrates Prior to Matrix-Assisted Laser Desorption-Ionization Time-of Flight Mass Spectrometry, Analytical Biochemistry, vol. 238, pp. 82-92 (1996).

* cited by examiner

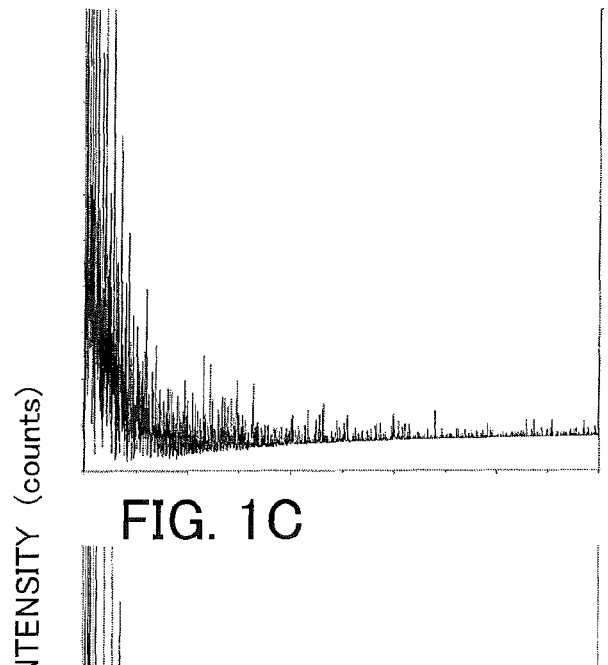
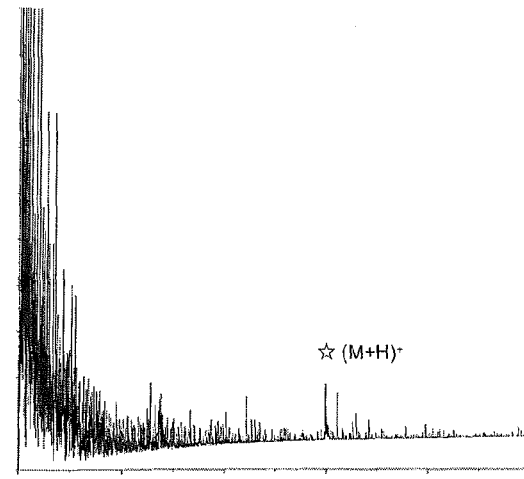
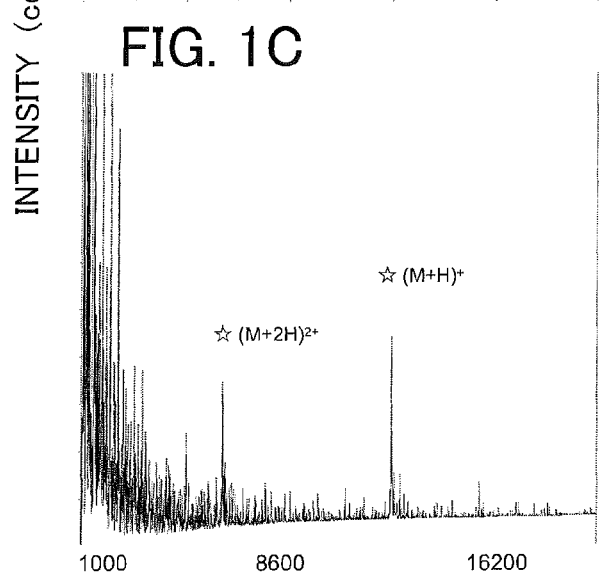
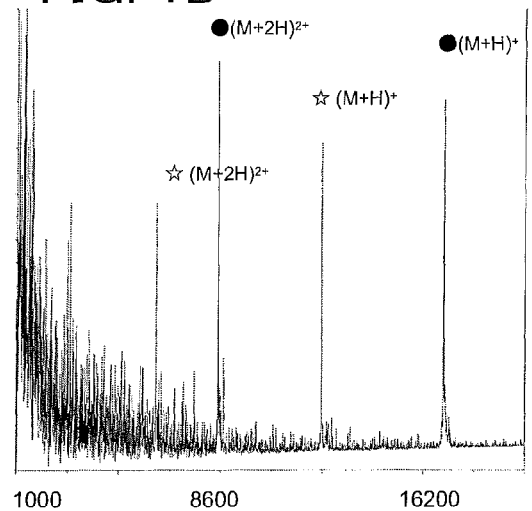

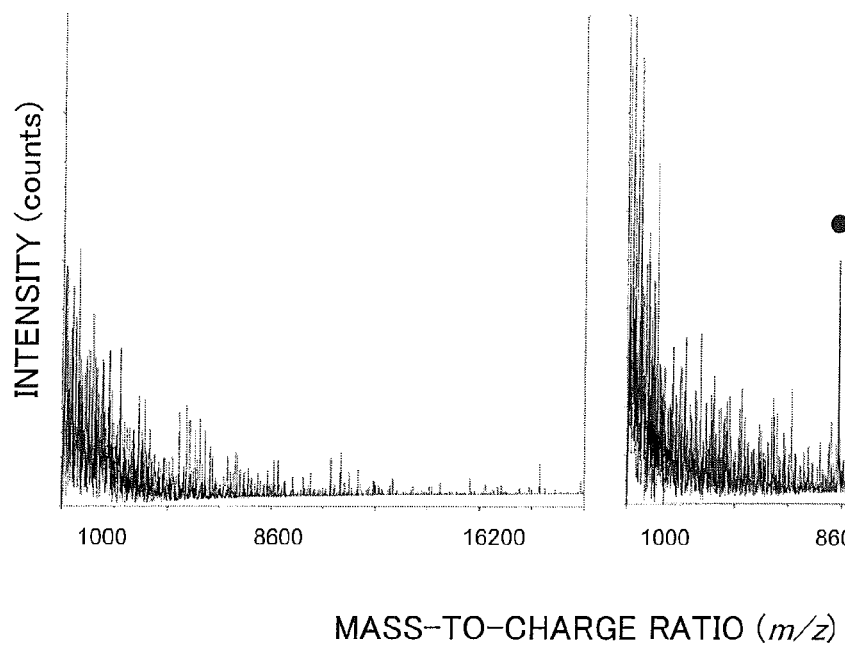
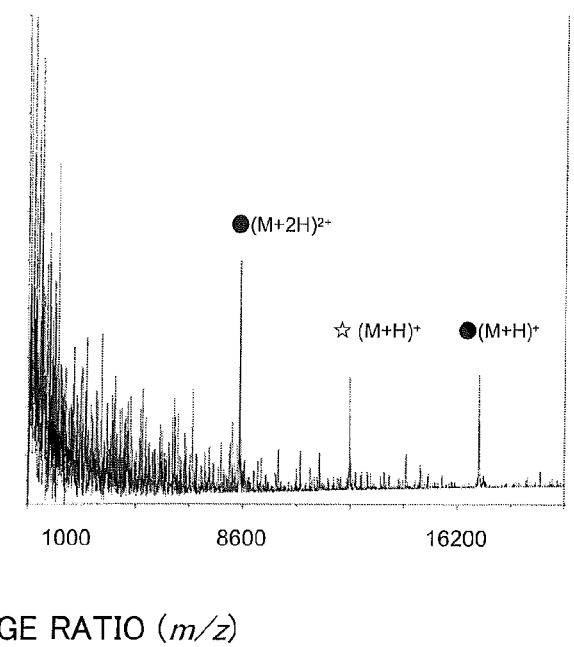

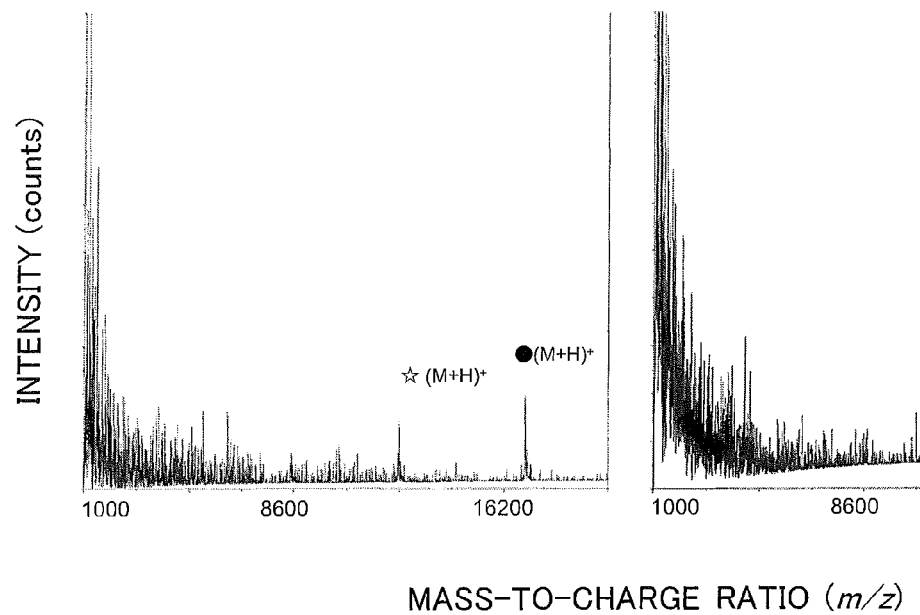

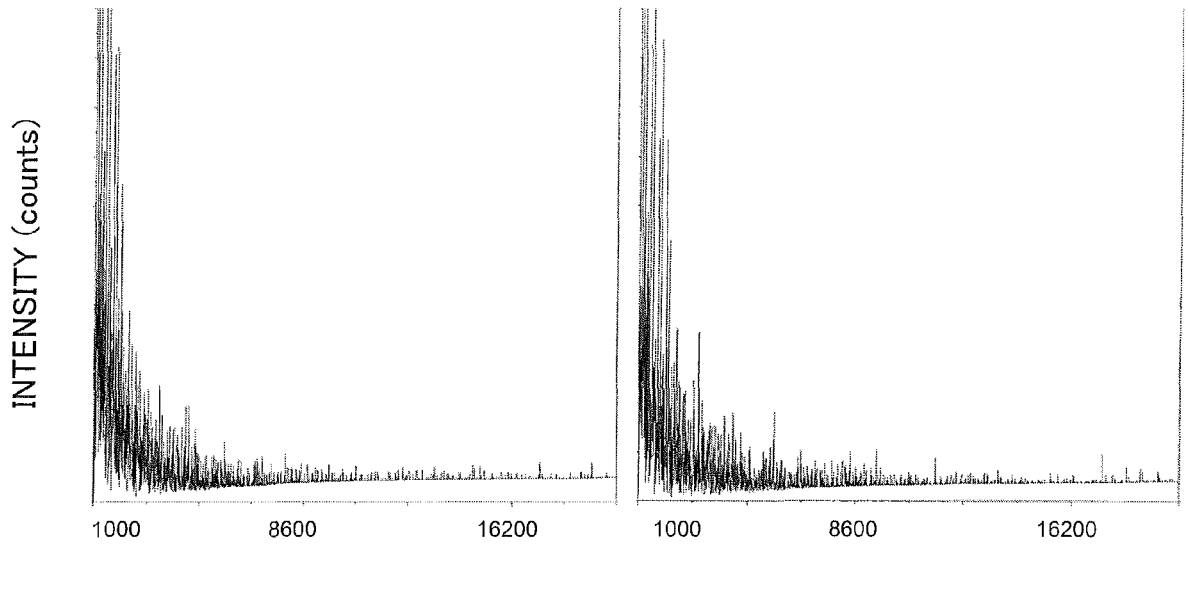

METHODS OF PREPARING SAMPLES FOR MALDI MASS SPECTROMETRY AND REAGENT COMPOSITIONS FOR THE SAME

This application is a continuation of International Application PCT/JP2006/300002, filed on Jan. 4, 2006, and claims priority to Japanese Patent Application No. 2005-002954, filed on Jan. 7, 2005, both of which are incorporated herein by reference in their entireties.

TECHNICAL FIELD

The present invention relates to a method of preparing a sample for matrix-assisted laser desorption/ionization mass spectrometry (MALDI-MS) and a reagent composition for conducting this sample preparation.

BACKGROUND ART

In this post-genomic era, a comprehensive research of proteins becomes more and more important, and a rapid and accurate technology for identifying a protein is needed. One of methods employed by many researchers is a technology for isolating an intended protein from various proteins by two-dimensional gel electrophoresis followed by analyzing the protein by mass spectrometry. With respect to the methods of mass spectrometry, development of an electrospray ionization (ESI) method and a matrix-assisted laser desorption/ionization (MALDI) method resulted in an establishment of a soft ionization technology of biopolymers, which leads to an innovative advancement of a proteomics research.

In MALDI mass spectrometry, a high molecular weight sample such as a protein is mixed with a matrix (for example, sinapinic acid) and subjected to a co-crystallization. The matrix serves to absorb a laser light and transfer its energy to the high molecular weight sample. The high molecular weight sample is ionized and typically produces an ion species of a $(M+H)^+$ type. Through this soft laser desorption process, the high molecular weight sample transfers into a gas phase. In the case of a time of flight (TOF) detector, upon ionization of the high molecular weight sample, the ion is accelerated in the electric field, and then arrives at the detector, where the time span from the ionization and the detection is measured and calculated at a high accuracy. The mass can accurately be calculated since the time of flight of an ion depends on the momentum, the square root of the mass-to-charge ratio (m/z).

In an ESI method, a liquid containing a high molecular weight sample eluted from a high pressure liquid chromatography (HPLC) column or a syringe pump at a microvolume/time is nebulized and injected into an electrospray ion source to effect an ionization. The ESI method is becoming a main stream of the proteomics analysis since its sample preparation is automated in advance of the MALDI method.

On the other hand, as a method for preparing a sample for the MALDI method, it is mainly employed to prepare a co-crystal with a matrix on a target plate after purifying the sample by a simple chromatography using reverse phased particles. However this method requires a technical skill and involves significant problems for attempting automation. Alternatively, there is a report that the surface of the target plate is modified with a self-assembled monolayer and impurities are removed on the target plate (for example, see non-patent references 1 and 2). Any of these methods is based on the concept that the impurities are removed before forming a co-crystal of the sample with a matrix. In addition, a method in which a chromatography medium is added for the purpose of removing salts mainly on a target plate (for example, see non-patent reference 3), or a two-layer method in which on a lower matrix formed using a reagent capable of ion-pairing with SDS an upper matrix is formed using an SDS-containing sample (ion-pair assisted recovery, for example, see non-patent reference 4), but any of these may fail to show a sufficient effectiveness due to a complicated operation and an inapplicability to an automation, and a further convenient and effective sample preparation method is required.

Non-Patent Document 1: Adam H. Brockman, Brian S. Dodd and Ron Orland, Anal. Chem., 69, 4716-4720 (1997)
Non-Patent Document 2: Maria E. Warren, Adam H. Brockman and Ron Orlando, Anal. Chem., 70, 3757-3761 (1998)
Non-Patent Document 3: Jason C. Rouse and James E. Vath, Analytical Biochemistry 238, 82-92 (1996)
Non-Patent Document 4: Rajendram V. Rajnarayanan and Kuan Wang, J. Mass Spectrum. 39, 79-85 (2004)

SUMMARY OF THE DISCLOSURE

The following analysis is given by the present invention. The entire disclosures of the above mentioned Non-Patent Documents are herein incorporated by reference thereto.

A most concerned issue in mass spectrometry is an ion suppression by impurities such as inorganic salts and detergents contained in a sample. A method for removing the impurities prior to the sample preparation for mass spectrometry by extensively purifying an analyte is not only laborious and time consuming but also associated with the following problems. For example, since a washing step is required after adsorption onto a silica gel, the sample is lost due to the removal of an analyte together with impurities during the washing step, which leads to a reduced sensitivity, resulting in a problematically reduced analytical accuracy.

The invention has been accomplished to solve the problems discussed above, and the object of the invention is to provide a method capable of giving high quality mass spectra by means of a simple operation on a target plate without conducting any washing step in preparing a sample for MALDI-MS containing a detergent such as SDS.

Thus, an inventive method of preparing a sample for matrix-assisted laser desorption/ionization mass spectrometry (MALDI-MS) is characterized in that an analyte of interest and a matrix molecule are subjected to a co-crystallization in the presence of a porous microparticle. The co-crystallization is performed preferably by contacting an analyte of interest, a matrix molecule and a porous microparticle on a target plate, and then drying a mixture thereof.

In one example of the invention, the porous microparticle is an ion exchanger that has a mean particle size of not more than 50 μm, and is preferably a strong anion exchanger. A preferred example of the strong anion exchanger is a granular silica gel modified by quaternary ammonium group or a vinyl polymer modified by quaternary ammonium group.

In one example of the invention, the sample comprises an analyte of interest, a matrix molecule and one or more salts or detergents.

In another aspect of the invention, a reagent composition for the preparation of a sample for the measurement by matrix-assisted laser desorption/ionization mass spectrometry (MALDI-MS) comprising a matrix molecule and a porous microparticle. As one example of such a reagent composition, the porous microparticle is in a state of suspension in a matrix solution. Alternatively, the matrix molecule and the porous microparticle may be dispensed in separate containers, and then mixed with each other immediately before use.

In a still another aspect of the invention, a method for analyzing a biopolymer substance containing a detergent such as SDS by preparing a sample by the abovementioned sample preparation method or using the abovementioned reagent composition and then analyzing it by a matrix-assisted laser desorption/ionization mass spectrometry (MALDI-MS).

The meritorious effects of the present invention are summarized as follows.

According to the method of the present invention, a MALDI-MS measurement can be conducted in a simple procedure without any loss of sample, since there is no need to purify an analyte preliminarily to a high purity. Although the MALDI-MS is suitable for a rapid measurement of a large number of samples since it can ionize a sample by a laser irradiation, it posed various problems at a stage of the co-crystallization of an analyte with a matrix because of which an automated measurement was difficult. Especially, the method of the present invention can be applied to an ionization of a sample protein cut out of an electrophoresis gel, which is an essential step in the field of a proteome analysis.

Also since the reagent composition of the present invention contains a porous microparticle, it allows, upon being mixed with an analyte, the sample to be dispersed uniformly whereby allowing a uniform co-crystal to be prepared on a target plate. A co-crystal of the analyte and the matrix molecule dispersed uniformly can readily be ionized by a laser irradiation, allowing a high quality mass spectrum to be obtained by a simple operation.

BRIEF DESCRIPTION OF THE DRAWINGS

FIGS. 1A to 1D show effects of the addition of 10 μm granular silica gels on MALDI mass spectra in the presence of 2.5% SDS. Results were shown with no additive (FIG. 1A), silica gel (FIG. 1B), cation exchange silica gel (FIG. 1C), and anion exchange silica gel (FIG. 1D). The symbol ☆ indicates cytochrome c and the symbol ● indicates myoglobin.

FIGS. 2A and 2B show a MALDI mass spectrum (FIG. 2A) in the presence of 5% SDS, and an effect of dilution with water thereon (FIG. 2B). The symbol ☆ indicates cytochrome c and the symbol ● indicates myoglobin.

FIGS. 3A and 3B show a difference in the effect between an ion exchanging group Q (FIG. 3A) and DEAE (FIG. 3B) on MALDI mass spectra in the presence of 1% SDS. The symbol ☆ indicates cytochrome c and the symbol ● indicates myoglobin.

FIGS. 4A and 4B show the effect of the addition of a spherical particle (FIG. 4A: average particle size 5 μm, FIG. 4B: average particle size 10 μm) in the presence of 2.5% SDS.

PREFERRED MODES OF THE INVENTION

Definitions

As used herein, the term "target plate" means an equipment having a site (spot) where a sample is held for MALDI-MS, and is sometimes simply referred to as "plate" or "sample plate". The target plate is not limited particularly as long as it can be used in mass spectrometry by a MALDI method, and may be a commercially available metallic or plastic one. In one example, an inventive target plate is made preferably from a metal capable of being washed extensively, such as a stainless steel, or may be a plate whose surface is protected by plating it with platinum or gold.

As used herein, the term "porous microparticle" means a particle whose surface area is sufficiently large and which allows selected molecules such as salts, solvent and detergent to penetrate into or adsorb on its inside while keeping other selected molecules such as analytes and matrix molecule on its surface. Specifically, it includes a silica gel and a zeolite. It allows the analyte to be concentrated on the surface of the particle while introducing low molecular weight impurities such as salts and detergents into the pores of the particle.

The term "ion exchanger" is one example of the abovementioned "porous microparticle", and is a common name referring to a substance exhibiting an ion exchange phenomenon. A representative includes an ion exchange resin, an ion exchange membrane, an ion exchange cellulose and the like. Those which can also be exemplified for cation exchange are naturally occurring materials such as zeolites, acidic white clay, peat, lignite and the like as well as synthetic zeolites, permutite, zirconium tungstate and the like, and also for anion exchange, those exemplified are a basic dolomite and gels such as hydrated iron oxide and hydrated zirconium oxide. The term "ion exchange resin" is a common name referring to an insoluble porous synthetic resin having ions capable of being exchanged.

(Method for Preparing Sample for Mass Spectrometry)

In the first aspect, the invention relates to a method for preparing a sample for MALDI-MS. In this sample preparation method, instead of removing impurities by extensively purifying an analyte when mixing the analyte and a matrix molecule to conduct a co-crystallization, adding a porous microparticle and allowing it to coexist in the sample to prevent the adverse effect of the impurities whereby promoting the ionization of the analyte intentionally. Such an analyte may for example be a biological high molecular weight substance such as proteins, peptides, nucleic acids and the like, and is preferably a protein or a peptide whose molecular weight is 1000 or more.

On the other hand, a matrix molecule in a positive ion mode may for example be, but not limited to, sinapinic acid, α-cyano-4-hydroxycinnamic acid, ferulic acid, gentisic acid, 3-hydroxypicolinic acid, 2,5-dihydroxybenzoic acid and the like. All of these compounds employed in the matrix are acidic substances. If much irradiation energy can efficiently be supplied to the ionization by ensuring a large surface area of the matrix co-crystal, a spectrum having a higher S/N ratio may be obtained. We focused on the fact that the matrix is acidic, and assumed that if a co-crystal is formed together with a porous microparticle such as an anion exchanger then a film of the co-crystal can be formed on this acidic surface. While an ordinary matrix co-crystal is spread two-dimensionally over a target plate, a three-dimensional spread can be accomplished if the co-crystal film is formed on the surface of the anion exchanger and the surface area of the co-crystal film is expected to be increased dramatically. Thus, a larger number of molecules will receive the ionization energy. On the other hand, a combination of a basic matrix such as harmine and a cation exchanger is employed correspondingly. Since a porous particle once dispersed in the matrix solution will be dispersed uniformly upon being mixed with the analyte, a sample crystallized after evaporation of water from this mixture can be prepared as a uniform co-crystal of the analyte and the matrix molecule.

An inventive method can preferably be employed with a sample containing one or more salts or detergents as impurities. Such a salt or detergent is known to suppress the ionization on MALDI-MS remarkably under an ordinary condition. A typical example is sodium dodecyl sulfate (SDS). The SDS is a strong solubilizing agent for proteins, lipids and other biomolecules, and employed widely in the life science technologies. For example, it is used in separating a protein mixture by electrophoresis or chromatography. Other salts or detergents may for example be, but not limited to, sodium deoxycholate, CHAPS (3-[(3-cholamidopropyl)dimethylammonio]-1-propanesulfonate), octyl-β-D-glucopyranoside (OG) and a polyoxyethylene surfactant having a molecular weight of 1000 or less (for example, Triton X-100, Brij 30 and the like).

Reagent Compositions

In another aspect, the invention relates to a reagent composition for preparing a sample to be measured by MALDI-MS. This reagent composition contains a matrix molecule and a porous microparticle, and the porous microparticle employed for adsorption and removal of impurities may be any chromatographic support employed usually for purifying a protein, such as a silica gel, anion exchanger, cation exchanger and the like. It may be selected appropriately depending on the types of contaminating salt or a detergent, and a single porous microparticle may solely be employed or a combination of two or more may be employed.

A silica gel, which is most commonly employed as a chromatography support is a porous silica gel having a large number of pores on its surface. The particle may be in a spherical shape or may be granular (irregular shape), and a spherical one is employed mainly in an adsorption chromatography because of its higher column packing efficiency. The silica gel may have various functional groups bound to silanol groups on its surface, and the most commonly employed one is an ODS (octadecyl silica) gel having an alkyl chain of 18 carbon atoms ($C_{18}$) on the silica surface. The number of the carbon atoms in the alkyl group to be bound may be reduced such as in octyl group, butyl group, methyl group and the like. As a functional group, a phenyl group, diol group, nitrile group, amino group and the like may also be attached.

On the other hand, when an ion exchange group is attached to a silica gel, then strongly acidic ($-SO_3H$), strongly basic ($-N^+(CH_3)_3$), weakly acidic ($-COOH$), weakly basic ($-N(CH_2CH_3)_2$) ion exchangers may be obtained. An ion exchanging resin employing an organic polymer gel instead of a silica gel may be employed. Such a polymer gel is preferably a polymethacrylate, polyhydroxymethacrylate, polyvinyl alcohol gel and dextran.

Any of these porous microparticles is preferably a microparticle whose average particle size is at most 50 μm for the purpose of obtaining a large surface area, and more preferably the average particle size is 20 μm or less, particularly 10 μm or less. The shape and the uniformity of the particle is not limited particularly, and includes various shapes such as spherical, rod-like, granular form and the like, preferably a granular form (irregular shape), more preferably a granular silica gel modified with a quaternary ammonium group. The reason for this is not clear, but a molecular sieve effect that a detergent is adsorbed onto the irregularly shaped cavities on the particle surface or appropriately sized cavities between particles may be involved.

A matrix molecule contained in an inventive reagent composition is preferably a highly purified compound. For example, sinapinic acid recrystallized at least twice using a solvent such as acetonitrile can be used for a prolonged period, such as at least 6 months, in a solution of 50% acetonitrile and 0.1% trifluoroacetic acid (TFA). Accordingly, a reagent composition according to the invention in one example is provided as a suspension in a matrix solution in which the porous microparticle is highly purified. Alternatively, the porous microparticle and the matrix solution may be dispensed in respective separate containers. Furthermore, various matrix solutions and porous microparticles may be contained in a kit, and a matrix solution selected based on the nature of the analyte is added to a porous microparticle selected appropriately from various anion exchangers and cation exchangers to form a suspension, which is then admixed with a certain analyte to form a sample. Any of these reagent composition or kits may include an instruction describing a sample preparation method to obtain optimum mass spectrometry results.

Mass Spectrometry Method

In still another aspect, the invention relates to a method of mass spectrometry on an analyte of a protein containing a detergent such as SDS, wherein a sample is prepared by the method of the present invention and this sample is used to conduct a matrix-assisted laser desorption/ionization mass spectrometry (MALDI-MS). As a result, a high quality mass spectrum can be obtained without any washing step for purifying the analyte. Thus, the invention employs a co-crystallization of an analyte containing a detergent such as SDS using an inventive reagent composition directly followed by subjecting it to a MALDI-MS, thus providing a method for performing a MALDI-MS measurement without washing the analyte for example with water and without removing a porous microparticle.

EXAMPLES

The invention is further explained in more details in the following EXAMPLES which are not intended to restrict the scope of the invention.

Example 1

(1) Reagents

A sinapinic acid is purchased from TOKYO CHEMICAL INDUSTRY CO., LTD (TCI, Tokyo), and recrystallized twice using acetonitrile and prepared a solution of 10 mg/ml in 50% aqueous acetonitrile with 0.1% TFA. Myoglobin and cytochrome c were purchased from Sigma Co., Ltd and employed in the experiments without further purification. A solid-phase particle used included a Wakogel (trade mark) LC-SAX-10H (10 μm granular quaternary ammonium group-modified silica gel, Wako Pure Chemical, Osaka), Nucleosil (trade mark) 100-SB10 (10 μm spherical quaternary ammonium group-modified silica gel, GL-Science, Tokyo), Partisil (trade mark) 10 SCX (10 μm granular sulfonate group-modified silica gel, GL-Science, Tokyo), Partisil (trade mark) 10 (10 μm granular silica gel, GL-Science, Tokyo), Nucleosil (trade mark) 100-SB5 (5 μm spherical quaternary ammonium group-modified silica gel, GL-Science, Tokyo), TOYOPEARL Super Q-650S (20 to 50 μm spherical quaternary ammonium group-modified vinyl polymer, TOSO, TOKYO), TOYOPEARL DEAE-650S (20 to 50 μm spherical diethylamino group-modified vinyl polymer, TOSOH, TOKYO). The protein samples and solid phase particles (support) were used as being purchased. Samples to be measured were prepared by mixing a solution of 400 μM myoglobin and 40 μM cytochrome c (100 mM NaCl, 50 mM Tris-HCl) in 1:1 ratio with a solution of SDS at the concentrations of 20, 50, 100 and 200 mg/mL, respectively. Final concentrations were 200 μM myoglobin and 20 μM cytochrome c (50 mM NaCl, 25 mM Tris-HCl, 1, 2.5, 5, 10% SDS).

(2) Measurement

As a MALDI/TOF-type mass spectrometer, an Applied Biosystems Voyager DE-STR was used, to which a target plate was inserted and irradiated with a laser beam (laser power 1900, 100 shots). An identical experiment was repeated four times or more to ensure the reproducibility.

(3) Experimental Procedure

The target plate was washed ultrasonically in a pure water for at least 10 minutes, dried, and then 0.1 μl of the protein sample was spotted on the dried target plate. 0.5 μl of a 10 mg/ml sinapinic acid solution combined with a solid support (particle) (50 mg/mL) was added and allowed to dry at room temperature (25±2° C., 40 to 60%).

(4) Results and Discussion

The results of the measurement of various samples prepared in the presence of 2.5% SDS according to the above experimental method are shown in FIGS. 1A to 1D. FIG. 1A represents the spectra of myoglobin and cytochrome c subjected directly to the co-crystallization using the sinapinic acid, and no ion of these analytes was observed. In FIG. 1B, a tiny peak of cytochrome c was observed in the sample co-crystallized with the granular silica gel. FIG. 1C shows the results of the sample after co-crystallization with the granular cation exchanger Partisil (trade mark) 10 SCX, and indicates that the intensities of the ion peaks of cytochrome c was increased. FIG. 1D also shows the results of the sample after co-crystallization with the granular anion exchanger Wakogel (trade mark) LC-SAX-10H, which afforded the prominent ion peaks of cytochrome c. In addition, the ion peaks of myoglobin which had never been observed before was observed with excellent S/N ratios.

Next, in order to investigate the SDS concentration, a sample subjected to the co-crystallization using an anion exchanger Wakogel (trade mark) LC-SAX-10H in the presence of 5% SDS was measured, and no ion of the protein of interest was observed as shown in FIG. 2A. Accordingly, the sample was subjected to a 2-fold dilution with water and the experiment was repeated, and this time the ion was observed evidently as shown in FIG. 2B.

These results indicate that, even when an impurity such as SDS was present, a satisfactory ionization of the protein can be achieved in the presence of the chromatograph medium (porous microparticle), suggesting that there is a way different from that in the prior art which is based on the concept that in a MALDI-MS measurement the impurities (inorganic salts, detergents, other impurities) should be removed as extensively as possible to form neat matrix co-crystals. With focusing especially on the fact that, even when using a 10 μm granular silica gel, only that having a surface modified (functionalized) with a quaternary ammonium group was capable of allowing the ion of the protein of interest to be observed at a satisfactory S/N ratio even in the presence of a high concentration of SDS, we compared between the types of the basic functional groups, namely the quaternary ammonium group and a weak anion exchanging diethylaminoethyl (DEAE) group using TOYOPERAL Super Q-650S and TOYOPERAL DEAE-650S, respectively.

The results are shown in FIGS. 3A and 3B. FIG. 3A shows the case employing a quaternary ammonium (Q) as an ion exchanging group in the presence of 1% SDS, and allows the monovalent ions of the cytochrome c and the myoglobin to be found clearly. On the contrary, the diethylaminoethyl (DEAE) group similarly in the presence of 1% SDS gave the results shown in FIG. 3B. Accordingly, it was revealed that the quaternary ammonium group allows for the ionization of the protein of interest even in the presence of a higher concentration of SDS. Such a finding suggests that the ionization of the protein of interest can be promoted to a greater degree when the amount of the matrix molecules and impurity SDS adsorbed on the surface of the ion exchanger employed becomes greater. In fact, no ion was observed when we removed the ion exchanger using a spatula according to the method by Rouse et al. Thus, the formation of the matrix co-crystal film on the surface of the ion exchanger is strongly supported.

Next, we assumed that if the matrix co-crystal film is formed on the surface of the ion exchanger the surface area is increased and its effect is enhanced by using a further finer particle, and then we conducted an experiment using spherical particles of 5 μm (Nucleosil (trade mark) 100-SB5) and 10 μm (Nucleosil (trade mark) 100-SB10) (5 μm granular particle is not commercially available).

The results are shown in FIGS. 4A and 4B. The both exhibited the performance lower than that of a 10 μm granular particle Wakogel (trade mark) LC-SAX-10H. From these findings, it can be concluded that, even when the particle size is reduced to increase the surface area, no substantial effect is experienced and the markedly irregular shape such as granular or crushed is rather effective. Thus, it was revealed that in addition to the basic surface the particle shape contributes greatly to the ionization. On the irregularly shaped surface, a molecular sieve effect serves to allow a low molecular weight inorganic salt or detergent to be incorporated into the inside of the particle during the course of the crystallization. Accordingly, we assumed that the SDS concentration in the crystal film on the surface is reduced relatively, resulting in a utilization of the irradiation energy in promoting the ionization of the substance of interest. This assumption is supported by the fact that when only the SDS is ionized the cluster ions of the SDS are markedly reduced only in a sample containing a granular anion exchanger.

In conclusion, two important factors, i.e., a basic environment attributable to a strong anion exchanging group and an increased surface associated with a molecular sieve effect attributable to a granular particle, may serve to exhibit a great inhibitory effect on the ion suppression by SDS. In other words, an increase in the basic surface area leads to a high affinity of the matrix with sinapinic acid which is an acidic substance, and it means that the co-crystallization with a substance of interest is distributed throughout a silica gel particle whereby allowing an irradiated laser energy to be absorbed at a high efficiency. In addition, the molecular sieve effect attributable to the granular particle allows a low molecular weight impurities such as detergents to be enclosed inside of the particle, whereby possibly promoting the ionization of the substance of interest.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:
1. A method of preparing a sample for matrix-assisted laser desorption/ionization mass spectrometry (MALDI-MS), said method comprising;
    a first step of mixing a matrix molecule with porous, ion-exchange microparticles to obtain a mixture, and
    a second step of co-crystallizing an analyte of interest with said matrix molecule by contacting said analyte of inter- est with said mixture of said matrix molecule and said porous, ion-exchange microparticles on a target plate.

2. The method of claim 1, wherein said co-crystallization is performed by contacting an analyte of interest with said mixture of said matrix molecule and said porous, ion-exchange microparticles on a target plate, and then drying a mixture thereof.

3. The method of claim 1, wherein said porous, ion-exchange microparticles have a mean particle size of not more than 50 μM.

4. The method of claim 1, wherein said porous, ion-exchange microparticles are a strong anion exchanger.

5. The method of claim 4, wherein said strong anion exchanger is a granular silica gel modified by quaternary ammonium group, or a vinyl polymer modified by quaternary ammonium group.

6. The method of claim 1, wherein a sample comprising said analyte of interest comprises one or more salts or detergents.

7. The method of claim 6, wherein said salts or detergents comprises sodium dodecyl sulfate (SDS), sodium deoxycholate, CHAPS, octyl-β-D-glucopyranoside (OG), and a polyoxyethylene detergent having a molecular weight of more than 1000.

8. The method of claim 1, wherein said analyte of interest comprises a biopolymer substance.

9. The method of claim 8, wherein said biopolymer substance is selected from the group consisting of proteins and peptides having a molecular weight of more than 1000.

10. A reagent composition for the preparation of a sample for the measurement by matrix-assisted laser desorption/ionization mass spectrometry (MALDI-MS), said composition comprising a matrix molecule and porous, ion-exchange microparticles.

11. The reagent composition of claim 10, wherein said porous, ion-exchange microparticles have a mean particle size of not more than 50 μm.

12. The reagent composition of claim 10, wherein said porous, ion-exchange microparticles are a strong anion exchanger.

13. The reagent composition of claim 12, wherein said strong anion exchanger is a granular silica gel modified by quaternary ammonium group, or a vinyl polymer modified by quaternary ammonium group.

14. The reagent composition of claim 10, wherein said porous, ion-exchange microparticles are a suspension in a matrix solution.

15. The reagent composition of claim 10, wherein said matrix molecule and porous, ion-exchange microparticles are dispensed in respective separate containers.

16. A method of mass spectrometry on an analyte of biopolymer substance comprising a detergent, said method comprising,
preparing a sample by the method of claim 1, and
performing matrix-assisted laser desorption/ionization mass spectrometry (MALDI-MS) using said sample.

17. The method of claim 16, wherein said detergent comprises sodium dodecyl sulfate (SDS).

18. A method for preparing a sample for matrix-assisted laser desorption/ionization mass spectrometry (MALDI-MS), comprising,
a first step of mixing a mixture of matrix molecules and porous, ion-exchange microparticles, and
a second step of bringing the analyte of interest, said matrix molecules and porous microparticles into contact with each other on a target plate in order to co-crystallize said analyte with said matrix molecules,
thereby obtaining said sample for matrix-assisted laser desorption/ionization mass spectroscopy.

* * * * *